United States Patent
Winterberg et al.

(10) Patent No.: US 9,624,143 B2
(45) Date of Patent: Apr. 18, 2017

(54) PROCESS FOR PREPARING LINEAR BUTENES FROM METHANOL

(71) Applicants: Markus Winterberg, Waltrop (DE); Ted M Pettijohn, Magnolia, TX (US); Stephen Bowers, Aldershot (GB); Joerg Schallenberg, Dorsten (DE); Shahbaz Naeem, Marl (DE); Oliver Markus Busch, Recklinghausen (DE)

(72) Inventors: Markus Winterberg, Waltrop (DE); Ted M Pettijohn, Magnolia, TX (US); Stephen Bowers, Aldershot (GB); Joerg Schallenberg, Dorsten (DE); Shahbaz Naeem, Marl (DE); Oliver Markus Busch, Recklinghausen (DE)

(73) Assignee: EVONIK DEGUSSA GmbH, Essen (DE)

( * ) Notice: Subject to any disclaimer, the term of this patent is extended or adjusted under 35 U.S.C. 154(b) by 104 days.

(21) Appl. No.: 14/425,976

(22) PCT Filed: Aug. 28, 2013

(86) PCT No.: PCT/EP2013/067768
§ 371 (c)(1),
(2) Date: Mar. 4, 2015

(87) PCT Pub. No.: WO2014/037254
PCT Pub. Date: Mar. 13, 2014

(65) Prior Publication Data
US 2015/0246857 A1    Sep. 3, 2015

(30) Foreign Application Priority Data
Sep. 5, 2012    (DE) .................. 10 2012 215 757

(51) Int. Cl.
*C07C 6/04* (2006.01)
*C01B 3/34* (2006.01)
(Continued)

(52) U.S. Cl.
CPC .................. *C07C 6/04* (2013.01); *C01B 3/34* (2013.01); *C07C 1/20* (2013.01); *C07C 1/24* (2013.01);
(Continued)

(58) Field of Classification Search
None
See application file for complete search history.

(56) References Cited

U.S. PATENT DOCUMENTS 5,990,369 A    11/1999    Barger et al.
7,737,318 B2    6/2010    Santiago-Fernandez et al.
(Continued)

FOREIGN PATENT DOCUMENTS

WO    WO 2010/006832 A2    1/2010

OTHER PUBLICATIONS

International Search Report issued Nov. 20, 2013 in PCT/EP2013/067768.
(Continued)

*Primary Examiner* — Tam M Nguyen
(74) *Attorney, Agent, or Firm* — Oblon, McClelland, Maier & Neustadt, L.L.P.

(57) ABSTRACT

The invention relates to a method for producing linear butenes from methanol. The problem addressed is that of specifying such a method in which the methanol used is converted, to the largest possible extent, into butenes. The problem is solved by combining a methanol-to-propylene
(Continued)

Figure 1:
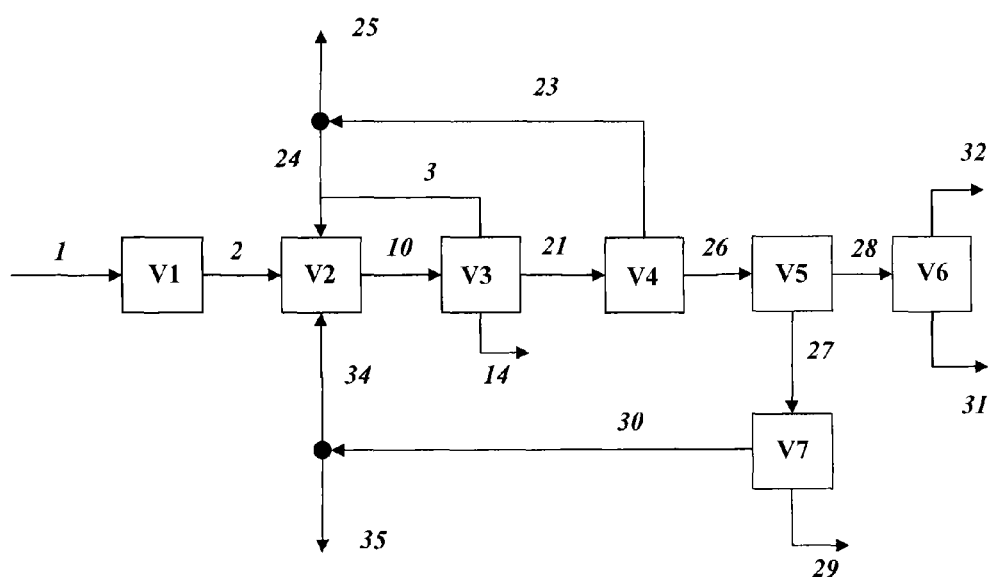

process with a metathesis reaction by means of which the propene obtained from the methanol is converted into linear butenes.

13 Claims, 5 Drawing Sheets

(51) Int. Cl.
    *C07C 1/20*     (2006.01)
    *C07C 1/24*     (2006.01)
    *C07C 2/26*     (2006.01)
    *C07C 29/151*     (2006.01)
    *C07C 41/09*     (2006.01)
    *C10J 3/82*     (2006.01)

(52) U.S. Cl.
    CPC .............. *C07C 2/26* (2013.01); *C07C 29/151* (2013.01); *C07C 41/09* (2013.01); *C10J 3/82* (2013.01); *C01B 2203/0205* (2013.01); *C01B 2203/061* (2013.01); *C07C 2523/28* (2013.01); *C07C 2523/30* (2013.01); *C07C 2529/06* (2013.01); *C07C 2531/02* (2013.01); *C10J 2300/093* (2013.01); *C10J 2300/0946* (2013.01); *C10J 2300/0973* (2013.01); *C10J 2300/1665* (2013.01); *C10J 2300/1853* (2013.01); *Y02E 50/32* (2013.01)

(56) References Cited

U.S. PATENT DOCUMENTS

| | | |
|---|---|---|
| 7,910,786 B2 | 3/2011 | Winterberg et al. |
| 7,919,662 B2 | 4/2011 | Winterberg et al. |
| 7,968,758 B2 | 6/2011 | Winterberg et al. |
| 8,633,345 B2 | 1/2014 | Winterberg et al. |
| 8,841,492 B2 | 9/2014 | Winterberg et al. |
| 8,940,951 B2 | 1/2015 | Winterberg et al. |
| 2008/0058572 A1 | 3/2008 | Fernandez et al. |
| 2010/0144998 A1 | 6/2010 | Santiago-Fernandez et al. |

OTHER PUBLICATIONS

Examination Report issued Nov. 17, 2016, in Australian Patent Application No. 2013311833 filed Aug. 28. 2013.

PROCESS FOR PREPARING LINEAR BUTENES FROM METHANOL

The invention relates to a process for preparing linear butenes from methanol.

Linear, unsaturated $C_4$-hydrocarbons such as 1-butene, cis-2-butene and trans-2-butene are sought-after starting materials and building blocks for many chemical products. These include, for example, polymers such as polybutene or polyethylene in which 1-butene is used as comonomer for LDPE or HDPE. Furthermore, the butenes are processed further by hydroformylation and subsequent hydrogenation to produce plasticizer alcohols such as isononanol (INA) or 2-propylheptanol (2PH). Subsequent esterification leads to PVC plasticizers such as diisononyl phthalate (DINP) or di-2-propylheptyl phthalate.

The $C_4$-hydrocarbons used today are obtained virtually exclusively from petroleum, either by steam cracking (cracking C4) or fluid catalytic cracking (FCC). However, refineries generally operate their crackers in accordance with the high demand for the $C_2$-hydrocarbons ethene and propene; the streams of higher hydrocarbons merely represent inevitable by-products. The availability of $C_4$-hydrocarbons is thus linked to developments in other markets. Due to increasing market success of products based on materials which come from the end of the value added chain from butenes, there is now such a great demand for butenes that it can barely be covered from the petrochemical source. This development forces the opening-up of new raw material sources.

One option which appears to be very advantageous is synthetic routes in which olefins are obtained from methanol by chemical reaction. These routes will hereinafter be referred to as "methanol to olefin process" (MTO).

MTO processes are known in the patent literature from WO01/92190A1, EP0448000B1 and DE19723363A1. However, the yield of linear butenes in these processes is rather low; for example, the butene yield in the process disclosed in EP0448000B1 is, based on the total amount of hydrocarbons produced, only about 30%. On the other hand, the process described in DE19723363A1 is optimized for a maximum propene yield, so that only small amounts of $C_4$-hydrocarbons are to be expected.

An overview of commercially operated MTO processes may be found in Process Economics Program Report 261 METHANOL TO OLEFINS, published in November 2007, obtainable from SRI Consulting. URL: http://www.ihs.com/products/chemical/technology/pep/methanol-to-olefins.aspx A specific MTO process is the methanol-to-propylene process (MTP process) in which methanol is reacted in two reaction steps, firstly to form dimethyl ether (DME) and this is then converted into propene and other olefins. The MTP process is offered commercially by LURGI. A more precise description of the LURGI-MTP process may be found in the abovementioned PEP report in section 5.1, pages 5-9. The MTP process produces the $C_3$-olefin propene but barely any $C_4$-olefins.

In the light of this prior art, it is an object of the present invention to provide a process for preparing linear butenes from methanol, in which a very large proportion of the methanol used is converted into butenes.

This object is achieved by a process according to Claim 1.

The invention accordingly provides a process for preparing linear butenes from methanol, which comprises the steps a to f:

a) provision of methanol;
b) reaction of the provided methanol in a first reaction stage to give a first reaction mixture containing dimethyl ether, water and possibly unreacted methanol;
c) reaction of dimethyl ether in a second reaction stage to give a second reaction mixture containing propene and also further hydrocarbons having two, four and five carbon atoms, where the second reaction stage is at least partly supplied with the first reaction mixture;
d) work-up of the second reaction mixture to give a propene-rich fraction and at least one low-propene fraction, where the low-propene fraction is at least partly recirculated to the second reaction stage;
e) reaction of propene in a third reaction stage to give a third reaction mixture containing ethene and linear butenes selected from the group consisting of 1-butene, cis-2-butene, trans-2-butene, where the third reaction stage is supplied at least partly with or from the propene-rich fraction;
f) work-up of the third reaction mixture to give a target fraction rich in linear butenes and an ethene-rich fraction.

This process is based on the idea of combining the MTP process with a third reaction stage in the form of a metathesis in which the propene obtained from the MTP process is converted into the desired linear butenes (1-butene, cis-2-butene and trans-2-butene).

The third reaction stage (metathesis) according to the invention can be carried out either in the presence or in the absence of propane. The background to these variants is that the saturated $C_4$-hydrocarbon propane has a similar boiling point to the more reactive $C_4$-olefin propene, as a result of which a propane/propene mixture is very difficult to separate industrially.

In the first variant, the metathesis is accordingly supplied with a propene-rich fraction which has previously been free of propane, so that the reaction in the third reaction stage occurs in the absence of propane. The propane is accordingly isolated as propane-rich fraction in the course of the work-up of the second reaction mixture.

However, it is industrially more advantageous to supply the third reaction stage with a propane-containing propene-rich fraction, so that the metathesis occurs in the presence of propane. Propane is inert in the metathesis. In this variant, the propane is isolated as propane-rich fraction from the third reaction mixture only after carrying out the third reaction step. This has the critical advantage that the propane-propene separation has to be carried out with a significantly smaller mass throughput since the propene is converted into $C_4$-hydrocarbons in the preceding metathesis. The separation of the low-boiling $C_3$ fraction containing the propane from the propene-containing $C_4$ fraction can then be carried out significantly more economically.

As regards the ethene formed in the metathesis, which is obtained in the ethene-rich fraction, the invention once again provides two alternative possible uses: firstly, it is possible to recirculate at least part of the ethene-rich fraction to the second reaction stage (the MTP reactor). The ethene is in this way reacted in the direction of propene.

As an alternative, the ethene can also be fed to a separate, fourth reaction stage in which a fourth reaction mixture comprising linear butenes from the group consisting of 1-butene, cis-2-butene and trans-2-butene is obtained. The fourth reaction stage is a dimerization. The separately carried out dimerization of ethene in the fourth reaction stage makes a further increase in the butene yield possible. The dimerization can also be carried out more selectively than the complex reaction in the MTP reactor (second reaction stage).

It is also possible to recirculate only part of the ethene-rich fraction to the second reaction stage and introduce the other part into the dimerization.

In a preferred embodiment of the invention, the step of the work-up of the second reaction mixture coming from the MTP reactor comprises isolation of a fraction rich in hydrocarbons having two carbon atoms, a fraction rich in hydrocarbons having four carbon atoms and a fraction rich in hydrocarbons having five carbon atoms. The work-up is carried out by distillation in an assembly of a plurality of distillation columns which separate off the respective $C_x$ fraction.

In the work-up, a $C_2$ fraction, a propene-rich $C_3$ fraction, a $C_4$ fraction and a $C_5$ fraction are thus obtained. The $C_2$ fraction contains predominantly ethene which is preferably recirculated to the second reaction stage (MTP reactor). The $C_5$ fraction can likewise be at least partly fed back into the second reaction stage. However, it is advisable to discharge part of the $C_5$-hydrocarbons as purge stream from the system in order to counter an unreasonable increase in concentration of high boilers.

The particular advantage of this complex work-up is that a $C_4$ fraction containing the sought-after butenes is obtained at the same time. The butenes are obtained not only in the metathesis (third reaction stage) but as early as in the MTP reactor (second reaction stage). These $C_4$-hydrocarbons obtained in the MTP reactor are isolated even before the metathesis during the course of the relatively complex work-up. The two $C_4$ streams can of course be mixed with one another and be jointly worked up further.

Furthermore, a high boiler fraction which contains the hydrocarbons having more than five carbon atoms should be obtained in the course of the work-up of the second reaction mixture. Such $C_{5+}$-hydrocarbons are generally referred to as high boilers and tend to accumulate in recycle processes. In order for the reaction not to be encumbered unnecessarily thereby, it is advisable to discharge the high boiler fraction from the process.

In the first reaction step, water is obtained in addition to the dimethyl ether (DME). This water of reaction is preferably likewise isolated as aqueous fraction during the course of the work-up of the second reaction mixture and discharged from the process. The dewatering of the second reaction mixture is preferably carried out by means of a quench. For this purpose, it is also possible to separate off an organic phase which contains unreacted methanol and DME. The organic phase is conveyed back into the second reaction stage.

The methanol used can have various origins. The basic chemical methanol is traded as a commodity and is therefore most simply purchased. It is also possible to prepare the methanol directly at the start of use or remotely therefrom. The in-house preparation of the methanol is particularly useful when the MTO process of the invention is operated at an integrated site. The preparation of methanol occurs according to process steps h to j:
  h) provision of a water-containing or water-free carbon source;
  i) preparation of synthesis gas containing carbon monoxide and hydrogen from the carbon source; if necessary with addition of water or water vapour;
  j) catalytic conversion of the synthesis gas into methanol in a fifth reaction stage.

These are conventional steps of methanol production. Details of the preparation of methanol may be found in Ullmann: Fiedler, E., Grossmann, G., Kersebohm, D. B., Weiss, G. and Witte, C. 2011. Methanol. Ullmann's Encyclopedia of Industrial Chemistry.

As carbon source, it is possible to use either a traditional fossil carbon source or a renewable raw material. Mixtures of fossil and renewable carbon sources can also be used. Suitable carbon sources are, in particular, hard coals, brown coals, petroleum fractions, oil sand, natural gas or shale gas. These are fossil sources. Renewable carbon sources can be utilized in the form of wood, biogas, biomass, domestic waste, manure or sewage sludge. The term biogas generally refers to a gas mixture which contains methane and has been produced by a biological route. Peat is at the transition between fossil and renewable carbon sources. However, particular preference is given to using shale gas for preparing the methanol. This is methane gas which is trapped in shale reservoirs and is released by injection of chemicals (fracking).

The first reaction stage (DME synthesis) is preferably carried out in the presence of a solid silica-alumina catalyst. This reaction is preferably carried out in the vapour phase, i.e. using gaseous methanol. The DME synthesis is known in the prior art and is described, for example, in EP0448000B1 and DE19723363A1. Details regarding the catalyst and the reaction conditions may also be found here.

The second reaction stage (MTP reaction), in which the methanol-water-dimethyl ether mixture from the first reaction stage is, optionally with addition of hydrocarbons recirculated from downstream process steps, reacted to form olefins, is preferably carried out over a shape-selective zeolite catalyst. For information regarding this step, reference is also made to the general prior art as is documented, for example, in EP0448000B1 or DE19723363A1.

In the third reaction stage, propene or a propene/propane mixture (both referred to as propene-rich fraction) is converted at least partly into linear butenes and ethene over a catalyst in the metathesis reaction. This generally proceeds according to the simplified reaction equation:

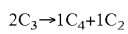

$$2C_3 \rightarrow 1C_4 + 1C_2$$

As metathesis catalyst, it is possible to use, for example, heterogeneous tungsten and/or molybdenum catalysts as are described, inter alia, in U.S. Pat. No. 3,340,322A or U.S. Pat. No. 3,261,879A.

Unreacted propene can, in a preferred embodiment, be separated off after the third reaction stage and recirculated to the metathesis. The ethene formed by the metathesis is isolated as ethene-rich fraction and then worked up to a high purity and marketed as further commercial product or is recirculated to the second reaction stage. The linear hydrocarbons formed in the metathesis are a mixture of essentially 1-butene, cis-2-butene and trans-2-butene. Depending on the reaction conditions selected and the catalyst system, the yield of 1-butene or the yield of 2-butenes can predominate.

In a further process variant, the ethene formed in the metathesis can be dimerized in a fourth reaction stage to form the desired butene. This reaction proceeds, for example, with high selectivity in the presence of a catalytic system composed of trialkylaluminium and alkyl titanate in ethers such as tetrahydrofuran. The selectivity of this reaction to 1-butene can be increased by adding the ether to the prepared mixture of trialkylaluminium and alkyl titanate. This is described, for example, in U.S. Pat. No. 4,532,370A. Alternative modes of operation and system in which predominantly 2-butenes are formed as product are known.

Figure 2:
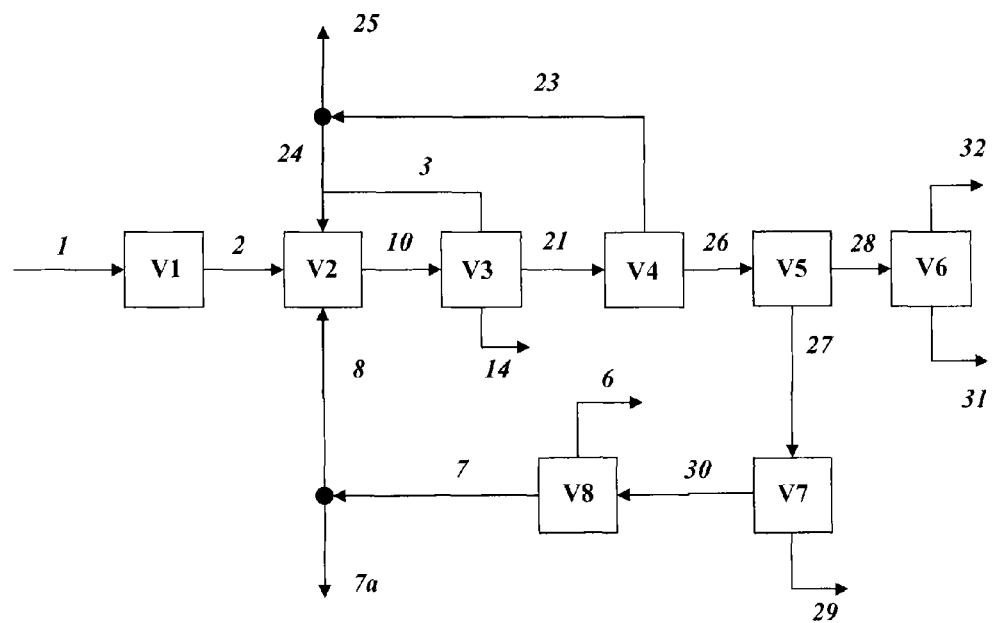
Figure 3:
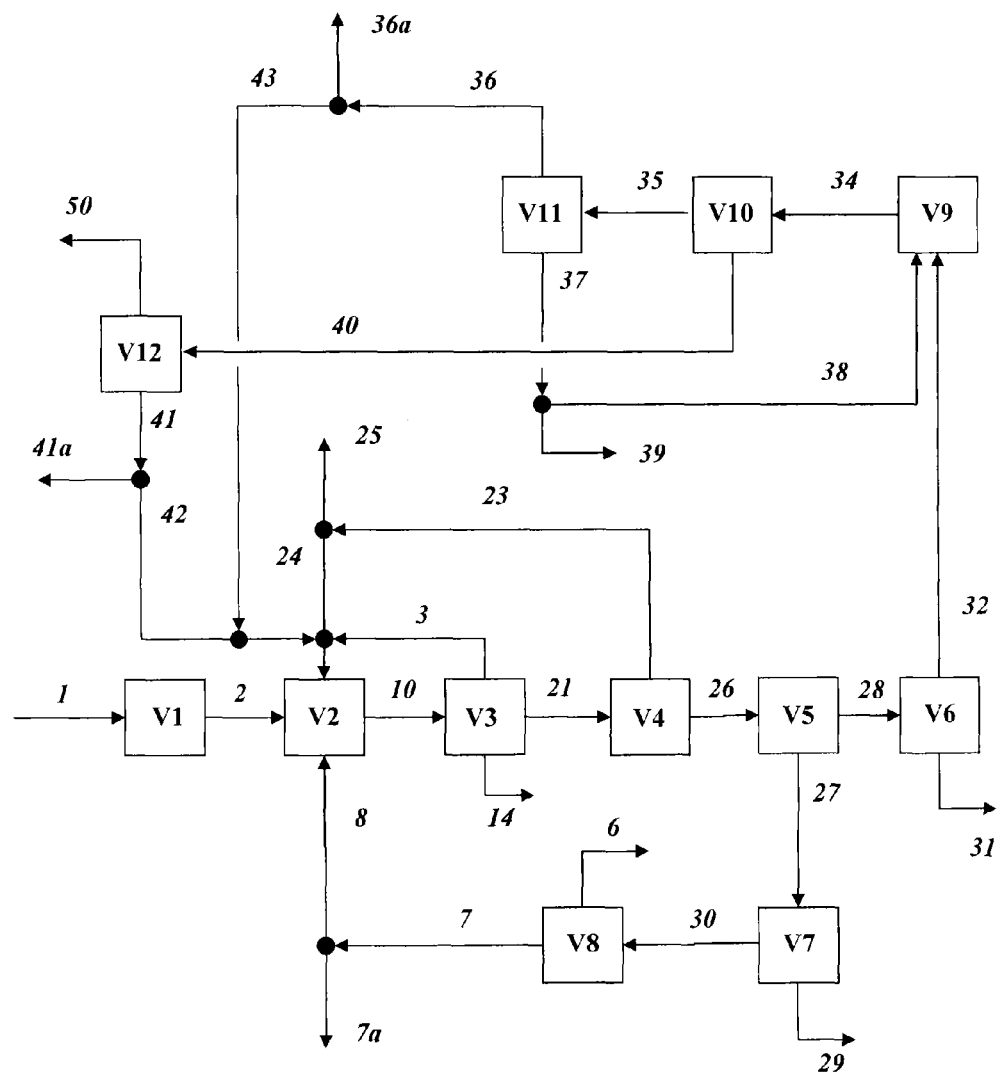
Figure 4:
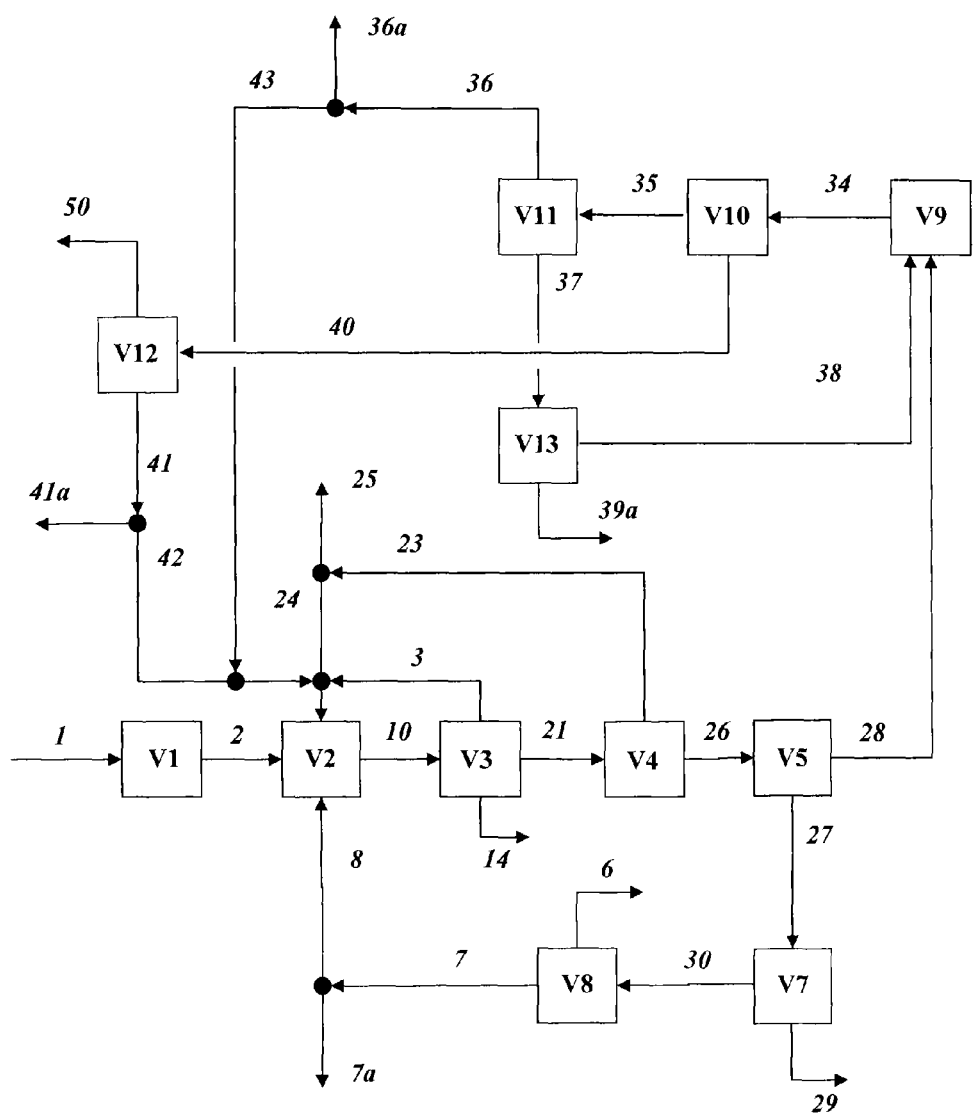
Figure 5:
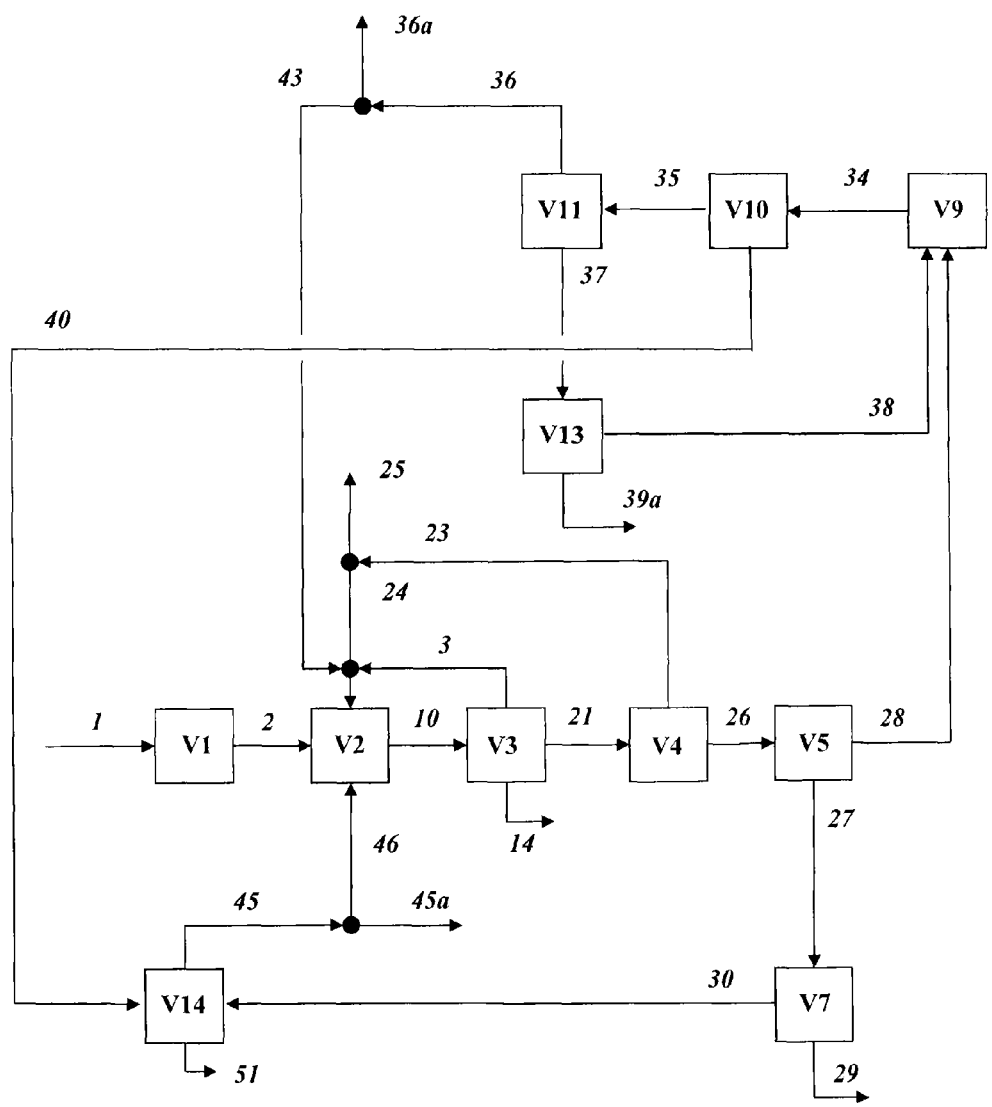

Various embodiments of the invention will now be illustrated with the aid of flow diagrams. For the purposes of improved clarity and comprehensibility, the flow diagrams have been reduced to the essentials. In particular, conveying devices and devices for altering pressure and temperature are not drawn in. The figures show:

FIG. 1: flow diagram of a conventional MTO process with recirculation of the $C_4$-hydrocarbons (prior art);

FIG. 2: flow diagram of a conventional MTO process with taking-off of the $C_4$-hydrocarbons (prior art);

FIG. 3: flow diagram of a first embodiment according to the invention with a propane-propene column installed upstream of the metathesis;

FIG. 4: flow diagram of a second embodiment according to the invention with a propane-propene column installed downstream of the metathesis;

FIG. 5: flow diagram of a third embodiment according to the invention with a propane-propene column installed downstream of the metathesis and only a single $C_4$-$C_5$ column.

A flow diagram of a conventional MTP process is depicted in FIG. 1. A stream of provided methanol (1) is, after heating and vaporization, fed into a first reaction stage (V1) for conversion of the methanol into dimethyl ether (DME). In a second reaction stage (V2), DME is completely or partly converted into olefins. For this purpose, the first reaction output (2), which contains at least DME, methanol and water, is, after further heating to the reaction temperature, fed into the second reaction stage (V2) for conversion of the DME and methanol into olefins. The streams (3), (24) and (34) are also recirculated to the second reaction stage (V2). In the second reaction stage (V2), the methanol still present, the DME and recycled components are converted into hydrocarbons. Water may also be involved in the reaction. The second reactor output (10), which contains at least DME, methanol, water and $C_1$-$C_6$-hydrocarbons, is, after cooling, fed to a process step (V3) in which the second reaction output (10) is quenched and water and an organic phase (13) containing unreacted DME, methanol and possibly residual water are separated off by distillation and phase separation. DME, water and methanol are recirculated as an organic fraction (3) to the second reaction stage (V2) and excess water is discharged as aqueous fraction (14). The remaining hydrocarbon mixture (21) is, after compression, separated by distillation in a low boiler column (V4) into an ethene-rich low boiler fraction (23) containing predominantly $C_1$- and $C_2$-hydrocarbons and a higher-boiling fraction (26) containing $C_3$-hydrocarbons and higher hydrocarbons. The low boiler fraction (23) is partly recirculated to the second reaction stage (V2). In order to avoid undesirable accumulation of by-products in the process, a purge stream (25) is discharged. The higher-boiling fraction (26) is separated by distillation in a $C_3$ column (V5) into a fraction rich in $C_3$-hydrocarbons (28) and a stream (27) which contains $C_4$-hydrocarbons and higher hydrocarbons. The $C_3$-rich fraction (28) is separated by distillation in a propane/propene column (V6) into a propene-rich fraction (32) containing virtually pure propene and a propane-rich fraction (31) which contains predominantly propane. The stream (27) is separated by distillation in a high boiler column (V7) into a relatively low-boiling fraction (30) containing predominantly $C_4$- and $C_5$-hydrocarbons and a high boiler fraction (29) containing $C_{5+}$-hydrocarbons, i.e. $C_6$-hydrocarbons and higher hydrocarbons. The relatively low-boiling fraction (30) is partly recirculated to the second reaction stage (V2). In order to avoid undesirable accumulation of by-products in the process, a purge stream (35) is discharged.

A flow diagram of a variant of a conventional MTP process is shown in FIG. 2. In this variant, the $C_4$-hydrocarbons are not recycled to the second reaction stage (V2) but instead are separated from the $C_5$-hydrocarbons (7) in a $C_4$ column (V8) and isolated as $C_4$-rich fraction (6). This contains, due to the process, a mixture and saturated and unsaturated $C_4$ isomers. The $C_4$ yield leaves something to be desired since the process is optimized for the production of $C_3$-olefins, namely propene (32).

A flow diagram of a first embodiment according to the invention of a plant in which the process of the invention can be carried out is shown in FIG. 3. In so far as this embodiment corresponds to the above-described MTP process, reference is made to the detailed description of FIGS. 1 and 2.

In this first embodiment according to the invention, a propene-rich fraction (32) together with the stream (38) are converted completely or partly into butenes and ethene and relatively small proportions of pentenes by metathesis in a third reaction step (V9). A third reaction mixture (34) from the metathesis (V9) is separated by distillation in a $C_3$ column (V10) into a stream (35) containing predominantly propene, propane and ethene and a stream (40) containing predominantly butenes and pentenes. In a $C_2$ column (V11), an ethene-rich fraction (36) containing predominantly ethene is separated off from stream (35). This gives a fraction (37) containing predominantly propene and propane. This is, after a purge stream (39) has been separated off in order to avoid accumulation of propane to undesirable concentrations, recirculated as propene-rich fraction to the metathesis (V9). The ethene-rich fraction (36) can, after a purge stream (36a) has been separated off, be partly recirculated to the second reaction step (V2).

In a $C_5$ column (V12), the butenes are separated off from higher-boiling components, predominantly pentenes formed in the metathesis. The $C_5$-rich fraction (41) can be completely or partly recirculated to process step (V2). The butene-rich fraction (50) contains predominantly linear butenes (1-butene and 2-butenes) and together with stream (6) represents the product of the process of the invention. To increase the yield of $C_4$-hydrocarbons further, partial recirculation of stream (36) can be omitted. Instead, this stream can optionally be fed to an ethylene dimerization. The ethylene dimerization takes place in a fourth reaction stage which is not shown in the figure. By-products from the dimerization can optionally also be recirculated to the second reaction stage (V2).

A flow diagram of a second embodiment according to the invention of a plant in which the process of the invention can be carried out is shown in FIG. 4. In this variant, a partial removal of propane (in process step (V6) in FIG. 3) is omitted. Instead, a propane-containing, propene-rich fraction (28) is fed directly to the metathesis (V9) and the latter is thus carried out in the presence of propane. In process step (V13), a propane-rich fraction (39a) is then separated off from the recycle stream (37) by distillation. This variant has the advantage over the variant in FIG. 3 that the outlay for separating off the propane (39a) from stream (37) is lower than from stream (28).

A flow diagram of a third embodiment according to the invention of a plant in which the process of the invention can be carried out is shown in FIG. 5. In this variant, the process steps (V8) and (V12) in the embodiment shown in FIGS. 3 and 4 are omitted. Hence, the $C_5$-hydrocarbons in streams (30) and (40) can be separated off from the target product, viz. the $C_4$-hydrocarbons, in only one process step (V14). This variant has the advantage over the variants shown in FIGS. 3 and 4 that the outlay in terms of apparatus for purification of the $C_4$-hydrocarbons is lower.

LIST OF REFERENCE SYMBOLS

V1: First reaction stage for conversion of methanol into DME
(Process step b): DME synthesis)
V2: Second reaction stage for conversion of DME into olefins
(Process step c): MTP reactor)
V3: Quench, isolation of water and recirculation of water, methanol and DME
V4: Low boiler column
(Isolation of $C_2$-hydrocarbons and lower-boiling components)
V5: $C_3$ column
(Isolation of $C_3$-hydrocarbons)
V6: Propane-propene column
V7: High boiler column
(Isolation of $C_{5+}$-hydrocarbons and higher-boiling components)
V8: $C_4$ column
V9: Third reaction stage for conversion of propene into olefins
(Process step e): metathesis reaction)
V10: $C_3$ column
(Isolation of $C_3$-hydrocarbons and lower-boiling components)
V11: $C_2$ column
V12: $C_5$ column
V13: Propane-propene separation
V14: $C_4$-$C_5$ separation
1: Methanol
2: First reaction mixture from V1, mixture of, inter alia, methanol, DME, water
3: Recycle stream into V2, mixture of, inter alia, methanol, DME, water
6: $C_4$-rich fraction containing, inter alia, 1-butene, 2-butenes, n-butane
7: $C_5$-hydrocarbons
7a: $C_5$-hydrocarbons
8: $C_5$-hydrocarbons
10: Second reaction mixture from V2, mixture of, inter alia, methanol, DME, water, hydrocarbons
14: Water discharge (quench)
21: Hydrocarbon mixture, including $C_1$-$C_6$-hydrocarbons
23: Low boiler fraction containing, inter alia, methane, ethene, ethane
24: Hydrocarbon mixture, including methane, ethene, ethane
25: Purge stream composed of low boilers, including methane, ethene, ethane
26: Relatively high-boiling fraction containing, inter alia, $C_3$-$C_6$-hydrocarbons
27: Hydrocarbon mixture, including $C_4$-$C_6$-hydrocarbons
28: $C_3$-hydrocarbons (propene, propane)
29: High boiler fraction, $C_{5+}$-hydrocarbons and higher-boiling components
30: Hydrocarbon mixture, including $C_4$-$C_5$-hydrocarbons
31: Propane-rich fraction
32: Propene-rich fraction
34: Third reaction mixture from V9, including ethene, propane, propene, butenes, pentenes
35: Purge composed of ethene, propane, propene
36: Ethene-rich fraction
36a: Purge stream composed of ethene
43: Ethene
37: Propane, propene
38: Propane, propene
39: Propane, propene
39a: Propane-rich fraction
40: Butenes, pentenes
41: $C_5$-rich fraction containing, inter alia, pentenes
41a: Purge stream composed of pentenes
42: Pentenes
45: $C_5$-hydrocarbons
46: $C_5$-hydrocarbons
47: $C_5$-hydrocarbons
50: Butene-rich fraction (target fraction)
51: Butenes

The invention claimed is:
1. Process for preparing linear butenes from methanol, comprising:
a) reacting methanol in a first reaction stage to give a first reaction mixture containing dimethyl ether, water, and optionally unreacted methanol;
b) reacting dimethyl ether in a second reaction stage to give a second reaction mixture containing propene and further hydrocarbons having two, four, and five carbon atoms, where the second reaction stage is at least partly supplied with the first reaction mixture;
c) working-up the second reaction mixture to give a propene-rich fraction and at least one low-propene fraction, where the low-propene fraction is at least partly recirculated to the second reaction stage;
d) reacting propene in a third reaction stage to give a third reaction mixture containing ethene and linear butenes selected from the group consisting of 1-butene, cis-2-butene, trans-2-butene, where the third reaction stage is supplied at least partly with or from the propene-rich fraction;
e) working-up the third reaction mixture to give a target fraction rich in linear butenes and an ethene-rich fraction,
wherein the propene-rich fraction contains propane,
wherein the reaction in the third reaction stage occurs in the presence of propane, and
wherein a propane-rich fraction is isolated during the course of working-up the third reaction mixture.
2. Process according to claim 1, wherein the ethene-rich fraction is at least partly recirculated to the second reaction stage.
3. Process according to claim 1, further comprising:
f) converting ethene into a fourth reaction mixture comprising linear butenes selected from the group consisting of 1-butene, cis-2-butene, trans-2-butene in a fourth reaction stage, where the fourth reaction stage is supplied from the ethene-rich fraction.
4. Process according to claim 1, wherein a fraction rich in hydrocarbons having two carbon atoms, a fraction rich in hydrocarbons having four carbon atoms, and a fraction rich in hydrocarbons having five carbon atoms are also isolated during the course of working-up the second reaction mixture, where the fraction rich in hydrocarbons having two carbon atoms and the fraction rich in hydrocarbons having five carbon atoms are at least partly recirculated to the second reaction stage.
5. Process according to claim 1, wherein a high boiler fraction containing hydrocarbons having more than five carbon atoms is also isolated during the course of working-up the second reaction mixture.
6. Process according to claim 1, wherein an aqueous fraction is also isolated during the course of of working-up the second reaction mixture.
7. Process according to claim 1, wherein, prior to the reacting:

preparing a synthesis gas containing carbon monoxide and hydrogen from a water-containing or water-free carbon source, and optionally with addition of water or water vapour; and in a fifth reaction stage, catalytically converting the synthesis gas into methanol for the reacting a).

8. Process according to claim 7, wherein the carbon source is a fossil carbon source, a renewable carbon source, or a mixture thereof, and wherein the carbon source is selected from the group consisting of: hard coal, brown coal, petroleum fractions, peat, natural gas, oil sand, shale gas, wood, biogas, biomass, domestic waste, manure, and sewage sludge.

9. Process according to claim 1, wherein the reaction in the first reaction stage occurs in the presence of a solid silica-alumina catalyst.

10. Process according to claim 1, wherein the reaction in the second reaction stage occurs in the presence of a zeolite catalyst.

11. Process according to claim 1, wherein the reaction in the third reaction stage occurs in the presence of a tungsten and/or molybdenum catalyst.

12. Process according to claim 11, wherein propene which has not reacted in the third reaction stage is separated off from the third reaction mixture and recirculated to the third reaction stage.

13. Process according to claim 3, wherein the reaction in the fourth reaction stage occurs in the presence of a catalytic system composed of trialkylaluminium and alkyl titanate in ethers.

* * * * *